United States Patent [19]

Meglan et al.

[11] Patent Number: 6,096,004
[45] Date of Patent: Aug. 1, 2000

[54] MASTER/SLAVE SYSTEM FOR THE MANIPULATION OF TUBULAR MEDICAL TOOLS

[75] Inventors: Dwight Allan Meglan, Lynnfield; Frederick Marshall Morgan, Quincy; Jeffrey Michael Wendlandt, Cambridge, all of Mass.

[73] Assignee: Mitsubishi Electric Information Technology Center America, Inc. (Ita), Cambrige, Mass.

[21] Appl. No.: 09/112,998

[22] Filed: Jul. 10, 1998

[51] Int. Cl.[7] .................................................. A61M 37/00
[52] U.S. Cl. ................................. 604/95; 901/34
[58] Field of Search .................. 604/95, 65–67; 600/106; 395/80–91; 318/568.11; 901/14–16, 34

[56] References Cited

U.S. PATENT DOCUMENTS

| | | | |
|---|---|---|---|
| 4,655,746 | 4/1987 | Daniels et al. | 604/53 |
| 5,631,973 | 5/1997 | Green | 382/128 |
| 5,791,908 | 8/1998 | Gillio | 434/262 |

*Primary Examiner*—Wynn Wood Coggins
*Assistant Examiner*—Eric Kline
*Attorney, Agent, or Firm*—Dirk Brinkman

[57] ABSTRACT

A master/slave system is used for performing a surgical procedure such as catheterization of cardiac or peripheral vasculature. Movements of catheters or similar tools within a patient are remotely controlled by a surgeon, and the surgeon receives haptic or tactile feedback caused by the movement of the tools within the patient. The system employs a master actuator with cylindrical controls and a slave actuator that engages the tools. The master actuator and slave actuator are electrically coupled to electrical interface circuitry by drive signals and sense signals. A fluid system is coupled to the slave actuator by fluid-carrying tubes for the delivery of contrast and other solutions to be injected into the vasculature for improved imaging and also to pressurize the balloon on a balloon catheter. The master and slave actuators contain sensors that sense translation and rotation of the controls and tools with respect to their longitudinal axes, and provide sense signals indicative of these motions to the interface circuitry. The master and slave actuators also contain motors respectively engaging the controls and tools to cause translational and rotational movement of these components in response to the drive signals generated by the interface circuitry. The interface circuitry contains a processor executing a master/slave control program via which the relative positions of each control and the corresponding tool are made to track each other. The control program can optionally implement force scaling, position scaling, tremor reduction, and other features to enhance the system's performance.

23 Claims, 11 Drawing Sheets

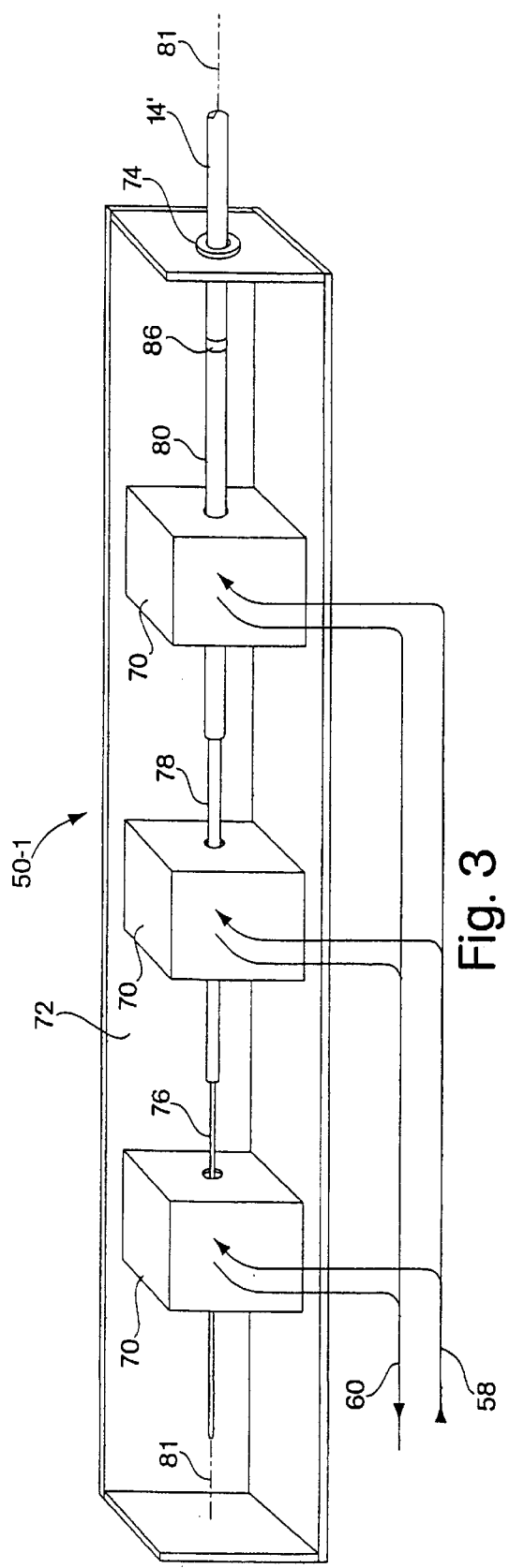
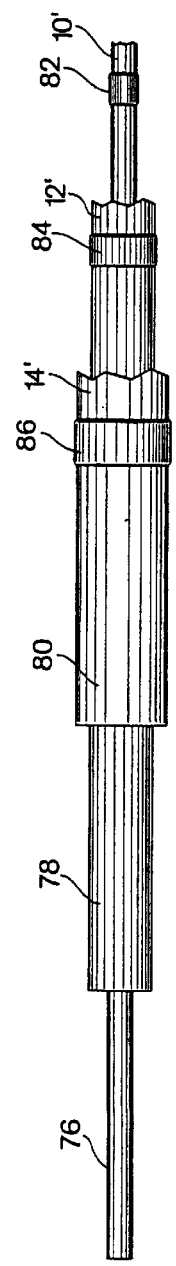
Fig. 3
Fig. 4

MASTER/SLAVE SYSTEM FOR THE MANIPULATION OF TUBULAR MEDICAL TOOLS

CROSS REFERENCE TO RELATED APPLICATIONS

None

STATEMENT REGARDING FEDERALLY SPONSORED RESEARCH OR DEVELOPMENT

Not Applicable

BACKGROUND OF THE INVENTION

The present invention is related to the field of master/slave control systems that enable a user to manipulate objects and that provide haptic or tactile feedback to the user, and more particularly to master/slave systems used for surgical procedures There is a trend toward increasing use of "minimally-invasive" surgical techniques, meaning techniques in which medical tools are inserted into a patient's body through a relatively small opening in the skin and manipulated from outside the body. In one example of a minimally invasive surgical technique known as "balloon angioplasty", concentric catheters are inserted into a patient's body and guided into a restricted blood vessel, such as a cardiac artery or a peripheral blood vessel suffering a blockage. One of the catheters, called a "balloon catheter" because it has a balloon-like inflatable chamber near the end, is guided into the blood vessel. The balloon-like chamber is inflated to stretch the vessel in the region of the blockage, so that the restricted passage is enlarged.

It is known to use master/slave control systems for some types of minimally-invasive medical procedures. Master/slave control systems are generally configured with a control that can be manipulated by a user, an actuator that holds a tool used in the procedure, and an electromechanical interface between the control and the tool. The electromechanical interface causes the tool to move in a manner dictated by the user's manipulation of the control. An example of a medical use of master/slave systems is in conjunction with an exploratory procedure known as "laparoscopy". During laparoscopy, a physician manipulates a control on a master device in order to maneuver an elongated camera-like device known as a "laparoscope" within the abdominal cavity. The movement of the laparoscope is actually effected by a slave device in response to signals from the master device that reflect the movement of the control by the physician. During the procedure, the physician receives visual feedback directly from the laparoscope. In addition to serving the diagnostic purpose of enabling the physician to examine the abdominal cavity, the visual feedback also enables the physician to properly maneuver the laparoscope.

Master/slave systems provide benefits that the direct manipulation of a surgical tool by a physician does not. Sometimes it is beneficial for the physician and patient to be physically isolated from each other, for example to reduce the risk of infection. A master/slave system may provide greater dexterity in the manipulation of small tools. Also, a master/slave system can be programmed to provide effects not achievable by a human hand. One example is force or position scaling, in which subtle movements on one end either cause or result from larger movements on the other end. Scaling is used to adjust the sensitivity of tool movement to movement of the control. Another example is filtering, such as filtering to diminish the effects of hand tremor or to prevent inadvertent large movements that might damage tissue.

In contrast to procedures such as laparoscopy in which the medical tool provides visual feedback, other minimally invasive procedures rely on other forms of feedback to enable a physician to maneuver a medical tool. For example, imaging apparatus is used in conjunction with balloon angioplasty to enable the physician to track the location of the end of the catheter or wire as it is threaded into an artery. This is also the case in interventional radiology. During these procedures the physician also receives tactile or haptic feedback via the tool itself, i.e. a catheter or wire. For example, the physician can feel frictional resistance if the catheter is being moved along the wall of an artery. Haptic feedback is an important component of the sensory information used by the physician to successfully carry out these types of procedures.

Master/slave systems have not been used in conjunction with procedures such as vascular catheterization or interventional radiology. Procedures such as these require very fine control over the movement of the tool within the patient, and also fine sensing of the subtle haptic feedback received via the tool. Heretofore these requirements have been met by the human hand interacting directly with the tool. However, it would be desirable to use master-slave control systems in such procedures, so that features such as force or position scaling and tremor reduction as discussed above can be taken advantage of.

BRIEF SUMMARY OF THE INVENTION

In accordance with the present invention, a master/slave control system for manipulating a generally cylindrical medical tool within a patient is disclosed that provides for fine control of tool movement by a user such as a physician, and also provides for fine sensing of the interaction of the tool with tissues within the patient. The system can be used for procedures such as peripheral vascular catheterization or cardiac catheterization in which the fine control and sensing are required, so that the benefits of using a master/slave system can be achieved for these procedures.

The disclosed apparatus includes at least one generally cylindrical control manipulated by a user so as to cause translation of the control along its longitudinal axis and rotation of the control about the longitudinal axis. A first actuator generates first electrical sensor signals from sensors coupled to the control, the first sensor signals being indicative of the translational and rotational movement of the control in response to the translation and rotation of the control by the user. Motors within the first actuator mechanically engage the control to cause translation and rotation of the control with respect to its longitudinal axis in response to selective application of first electrical motor drive signals to the motors. A second actuator generates second electrical sensor signals from sensors coupled to the tool, the second sensor signals being indicative of the translational and rotational movement of the tool with respect to its longitudinal axis. Motors within the second actuator mechanically engage the tool to cause translation and rotation of the tool with respect to its longitudinal axis in response to selective application of second electrical motor drive signals to the motors. An electronic interface receives the first and second electrical sensor signals as inputs, and generates the first and second motor drive signals to cause movement of the tool in response to movement of the control by the user and to provide haptic feedback to the user in response to movement of the tool inside the patient.

The invention is applicable to catheterization-like procedures in which an elongated tool is manipulated within a patient's body. Because translational and rotational movements are sensed and caused independently, the system enables a high degree of fidelity in the replication of the user's movement at the tool and the replication of the haptic feedback from the tool at the control. Additionally, the electrical interface enables the use of desirable effects such as force and position scaling, tremor reduction, and other effects to enhance the functionality of the system.

Other aspects, features, and advantages of the present invention are disclosed in the detailed description which follows.

BRIEF DESCRIPTION OF THE SEVERAL VIEWS OF THE DRAWING

FIG. 3 is a perspective diagram of a first embodiment of an actuator assembly for the system of FIG. 2 including schematically-depicted actuators;

FIG. 4 is a diagram showing the coupling between catheters and corresponding tubes in the actuator assembly of FIG. 3;

DETAILED DESCRIPTION OF THE INVENTION

Figure 1:
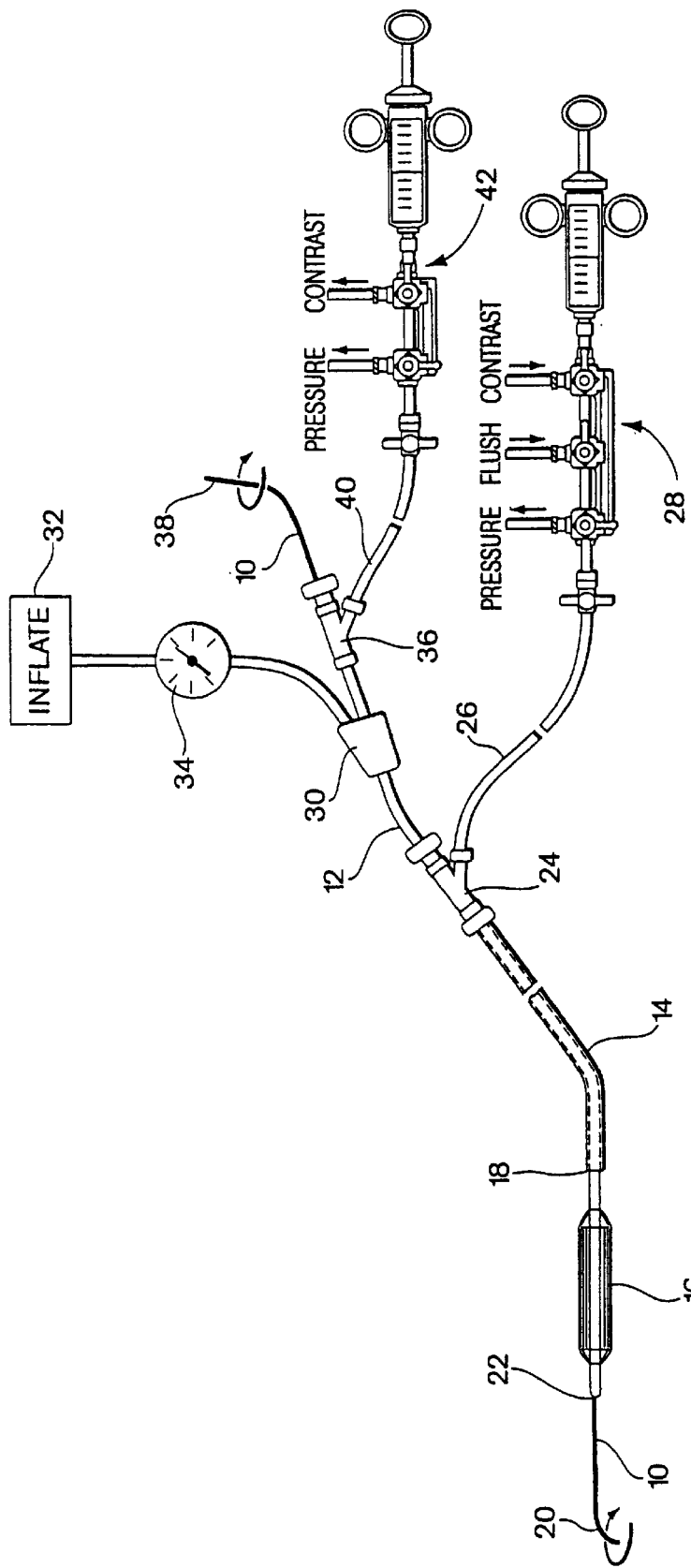
FIG. 1 is a schematic diagram of prior-art apparatus for catheterization of cardiac or peripheral vasculature including a set of concentric catheters.

FIG. 1 illustrates known apparatus for catheterization of cardiac or peripheral vasculature. As illustrated, the apparatus includes an inner wire 10, a tubular balloon catheter 12, and a tubular guide catheter 14. The balloon catheter 12 includes a dilatation balloon 16 at one end that extends beyond a corresponding end 18 of the guide catheter 14. The wire 10 has a tip 20 that extends beyond the end 22 of the balloon catheter 12.

A first Y adaptor 24 is secured to the guide catheter 14. The balloon catheter 12 extends through one leg of the Y adaptor 24, and tubing 26 is attached to the other leg. The tubing 26 carries contrast and other solutions into the guide catheter 14. The contrast solution enhances the visibility of the vessel being catheterized on imaging equipment used during the catheterization, process, enabling the doctor to better guide the catheter. The injection and flushing of the contrast and other solutions is controlled by apparatus 28 as is known in the art.

A coupling 30 enables the attachment of an inflation device 32 and associated pressure meter 34, as well as a second Y adaptor 36. A user end 38 of the wire 10 extends from one leg of the Y adaptor 36, and tubing 40 extends from the other leg. The tubing 40 is connected to contrast injection and flushing apparatus 42 used to provide contrast and other solutions to the balloon catheter 12.

In the embodiment of FIG. 1, the ends 20 and 38 of the wire 10 are bent slightly. At the user end 38, the bent section enables the wire 10 to be rotated about its longitudinal axis (also referred to herein as "axial rotation") by a doctor. At the inner or guide end 20, the bent section enables the wire 10 to be steered through turns and branches in the pathway to the vessel being catheterized.

During a balloon angioplasty procedure for a cardiac artery, the guide catheter 14 is first inserted into the femoral artery of a patient so that its end is at the aortic arch, near the opening of a cardiac artery to be operated upon. The guide catheter 14 arrives at this position by being slid along a previously-inserted guide wire (not shown), which is removed after the guide catheter 14 is in place. Next, the balloon catheter 12 and wire 10 together are pushed through the guide catheter 14 to its end. The wire 10 is then manipulated into the artery to the area to be dilated, and the balloon 16 is pushed along the wire 10 into the desired position. In this position the balloon 16 is inflated as necessary to achieve the desired dilation of the artery.

Figure 2:
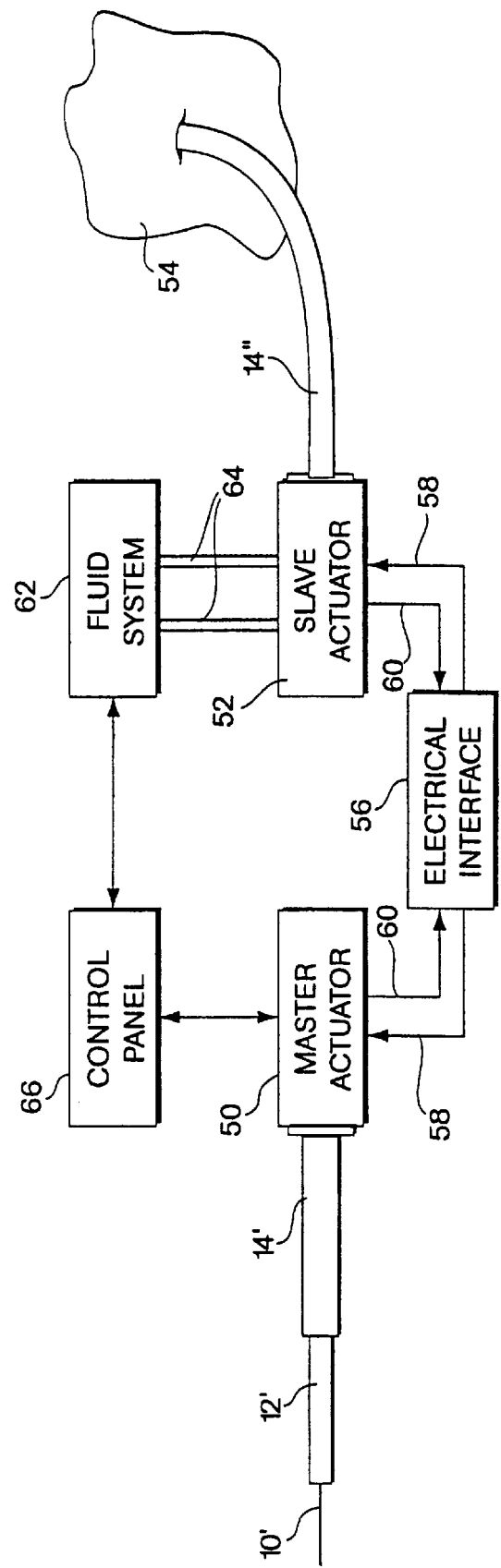
FIG. 2 is a schematic block diagram of a master/slave catheterization system according to the present invention.

FIG. 2 depicts a master/slave system for performing catheterization. The system employs catheter-like cylindrical controls 10', 12' and 14' that are part of a master actuator 50. A slave actuator 52 senses and controls the movement of a catheter 14", as well as a catheter 12" and a wire 10" not shown in FIG. 2, within a patient 54. The master actuator 50 and slave actuator 52 are electrically coupled to electrical interface circuity 56 by respective drive signals 58 and sense signals 60. A fluid system 62 is coupled to the slave actuator 52 by fluid-carrying tubes 64. Various system operations are controlled by a control panel 66. These operations include the injection of contrast and other fluids into the vasculature through the catheter 14, and into the balloon 16 in order to inflate it. The fluid system 62 includes electrically-operated valves responsive to control signals from the control panel 66. The system optionally performs a sequence of timed inflations of the balloon 16 in response to input at the control panel 66. This feature improvers upon prior methods of inflating the balloon 16 to enlarge the restricted opening.

The actuators 50 and 52 contain sensors that sense translation and rotation of the controls 10', 12' and 14' and the tools 10", 12" and 14" with respect to their respective longitudinal axes. Pulse signals 60 indicative of these motions are provided to the interface circuitry 56. The actuators 50 and 52 also contain motors respectively engaging the controls 10', 12' and 14' and the tools 10", 12" and 14". The motors cause translational and rotational movement of these components about their respective axes in response to the drive signals 58 generated by the interface circuitry 56.

The electrical interface circuitry 56 preferably includes electrical driver and amplifier circuits for the signals 58 and 60, and a processor coupled to these circuits. The processor executes a master-slave control program that uses information from the sense signals 60 to generate the drive signals 58 such that the catheters 12" and 14" and the wire 10" move within the patient 54 in a manner dictated by the controls 10', 12' and 14'. These movements include both translation and rotation with respect to the longitudinal axis of the corresponding catheter or wire. The master-slave control program is preferably of the type known as "position matching". In this type of control program, the signals 58 and 60 are used to ensure, if possible, that the relative positions of each control 10', 12' and 14' and the corresponding wire 10" or catheter 12" or 14" do not change. For example, assuming an initial position of control 14' and catheter 14", if a user pushes control 14' inwardly by one inch, the control program responds by pushing catheter 14" in by one inch. If the catheter 14" encounters an obstacle during this movement, a feedback force is generated on the control 14' that opposes the user's movement in an attempt to bring the position of the control 14' to the (blocked) position of the catheter 14".

One of the benefits of a master/slave control system is the ability to choose how the slave device responds to any particular input from the master device. For example, it is known to provide functions such as force or position scaling and tremor reduction. When force or position scaling are used, the slave responds to the master by applying a similar force or moving to a similar position, but scaled by some constant value. For example, in a system implementing 2:1 position scaling the slave would move one inch for every two inches of movement of the master. Scaling can also be applied in the other direction, from the slave to the master, and in fact the two are usually used together to achieve the full desired effect. Scaling enables a user to manipulate small tools while interacting with a much larger control on the master. Tremor reduction involves filtering the master input such that a pattern found to be periodic within a particular frequency band has a more attenuated affect on movement of the slave than do other types of movement. The electrical interface 56 optionally employs force or position scaling, tremor reduction, and other similar techniques that enhance the effectiveness of the master/slave system.

Another feature that may be enabled by the electrical interface 56 is the use of preprogrammed motion sequences. For example, in response to a signal from the control panel 66, the electrical interface 56 can cause the wire 10" to vibrate at a high frequency, much faster than is possible with the human hand in control. This vibratory motion can be used, for example, to free the wire 10" if it becomes stuck in a blood clot within the vessel. Depending on the application, the electrical interface 56 can optionally perform other types of preprogrammed sequences useful in particular situations that might arise during the procedure.

FIG. 3 shows a first embodiment of an actuator assembly 50-1 that can be used as either the master actuator 50 or the slave actuator 52 in the system of FIG. 2. Three actuators 70 are disposed on a base 72 within a housing. Although the actuators 70 are shown as boxes, this representation is schematic only; details of the actuators 70 are shown in FIGS. 5–9 described below. At one end of the base 72, the controls 10', 12' and 14' enter the base 72 at one end through a sleeve or grommet 74. A set of stiff concentric tubes 76, 78 and 80 are disposed in telescoping fashion through the actuators 70 along an actuation axis 81. As shown in. FIG. 4, the controls 10', 12' and 14' are connected to corresponding tubes 76, 78 or 80 by corresponding couplers 82, 84 or 86. The couplers 82, 84 and 86 may be pieces of tape, or more complicated automated mechanical devices that provide secure mechanical coupling between each of the corresponding tubes and the respective catheter.

The innermore tubes 76 and 78 each extend beyond their respectively adjacent outer tubes 78 and 80 in order to permit engagement by a corresponding one of the actuators 70. The amount by which each of the innermore tubes 76 and 78 extends beyond the corresponding outermore tube 78 or 80 is chosen to enable each tube to freely travel between a retracted position (toward the right in FIG. 3) and an extended position (toward the left in FIG. 3) without interfering with the travel of the other tubes. The retracted position corresponds to the initial position of the corresponding real wire 10 or catheter 12 or 14 upon being inserted into the patient; the extended position corresponds to the final position of the corresponding real wire 10 or catheter 12 or 14 after it has been pushed into the vicinity of the vessel being catheterized.

The actuators 70 are placed so that each one engages the corresponding tube 76, 78 or 80 throughout its travel and does not present an obstacle to the travel of the other tubes. Each actuator 70 senses the axial translation and axial rotation of the corresponding tube 76, 78 or 80 with sensors which are described below in greater detail. The sensors provide indications of axial translation and rotation via the sense signals 60. Each actuator 70 includes motors which are responsive to corresponding ones of the drive signals 58 to generate axial force and torque on the corresponding tube 76, 78 or 80. The actuators 70 are described in greater detail below.

Figure 5:
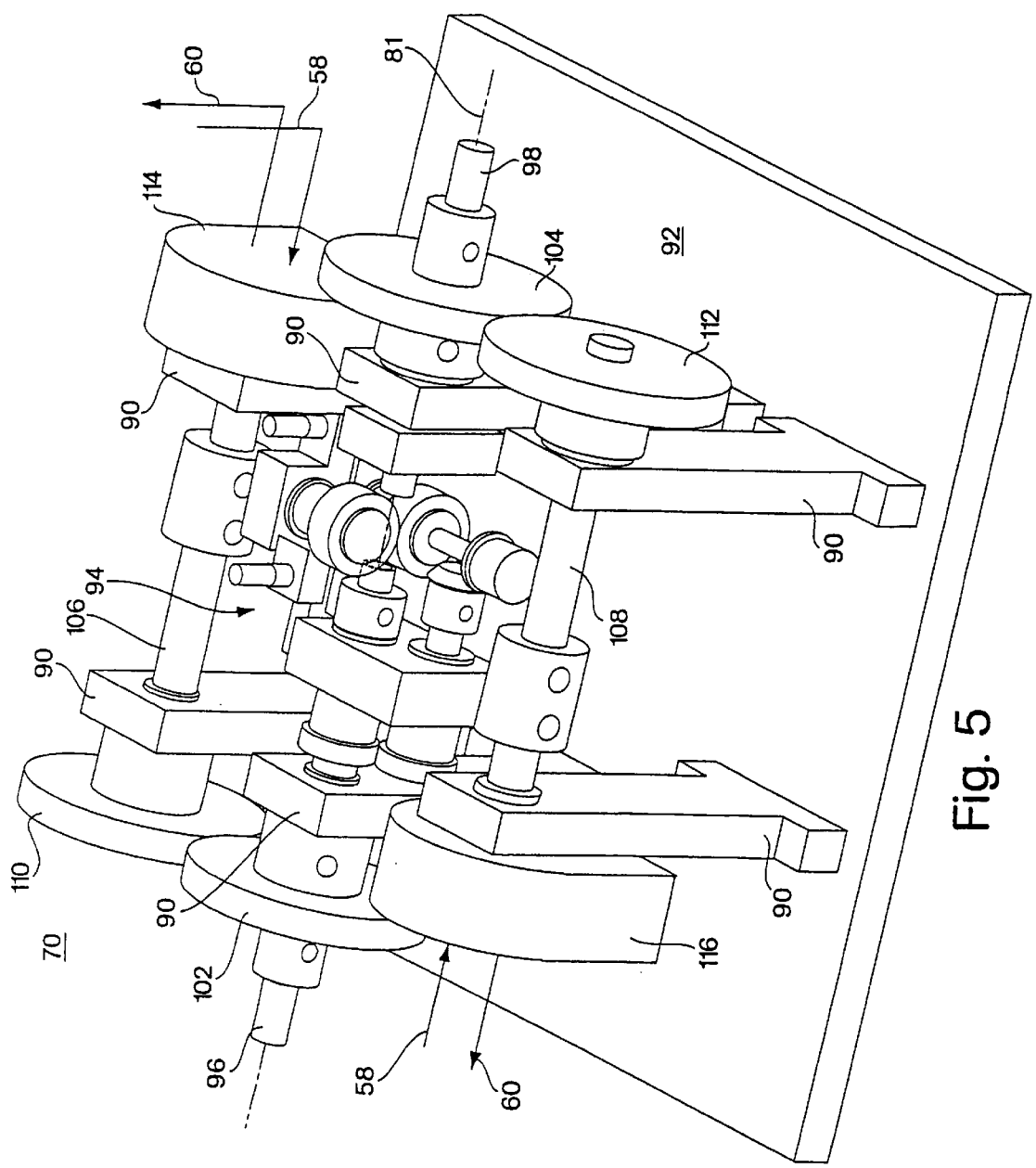
FIG. 5 is a perspective diagram of an actuator in the actuator assembly of FIG. 3.

FIG. 5 shows one embodiment of an actuator 70. Support pedestals 90 extend from a base 92. One pair of the support pedestals 90 supports a carriage assembly 94 via shaft segments 96 and 98 disposed through openings in the pedestals 90 along the actuation axis 81. Also supported on the shaft segments 96 and 98 are a translation control wheel 102 and a rotation control wheel 104. The carriage assembly 94 and rotation control wheel 104 are both secured to the shaft 98, so that rotation of the rotation wheel 104 causes rotation of the carriage assembly 94 about the actuation axis 81. The coupling between the translation control wheel 102 and the carriage assembly 94 is described in greater detail below with respect to FIG. 6.

Additional pairs of support pedestals 90 support drive shafts 106 and 108 in parallel with the actuation axis 81. Each drive shaft 106 and 108 extends through openings in the corresponding pair of support pedestals 90. Drive wheels 110 and 112 are mounted on the drive shafts 106 and 108, respectively. The drive wheel 110 engages the translation control wheel 102, and the drive wheel 112 engages the rotation control wheel 104.

Motor/sensor assemblies 114 and 116 are mechanically coupled to the drive shafts 106 and 108, respectively. Motors within the assemblies 114 and 116 apply torque to the corresponding drive shaft 106 or 108 in response to the drive signals 58. These motors are preferably direct-current (DC) torque motors. The sensor within each assembly 114 and 116 senses the rotational position of the corresponding co-located motor. The sensors may be conventional rotary position encoders or any other suitable devices. The sensors generate sense signals 60 indicating the sensed positions of the respective wheel 102 or 104. The signals 60 may be, for example, respective series of pulses, in which each pulse represents a quantum of rotation of the corresponding motor.

The signal 60 generated by the sensor within the assembly 116 indicates the rotational position of the tube disposed within the actuator 70. The signal 60 generated by the sensor within the assembly 114 provides both rotation and translation information, because of the configuration of the gears on the carriage assembly 94 as described below. Thus in order to obtain the translational position of the tube, the signal 60 from the assembly 114, which indicates purely rotation, is subtracted from the signal 60 from the assembly 116 indicating both rotation and translation.

During operation of the actuator 70 of FIG. 5, one of the tubes 76, 78 or 80 is disposed through the actuator 70 along the actuation axis 81. The user pushes, pulls, and rotates the tube. Pushing and pulling motions of the tube cause the wheel 102 to rotate, and rotation of the tube causes both wheels 102 and 104 to rotate. The rotation of the wheels 102 and 104 is detected by the encoders within the assemblies 114 and 116, and the values of the signals 60 generated by the encoders change correspondingly. The interface 56 of FIG. 2 receives the position information via the circuit 54. In accordance with the master/slave control program being executed, the interface 56 causes the drive signals 58 to take on values corresponding to the desired force and torque to be applied to the tube. These signals drive the motors within the assemblies 114 and 116. The motors apply the desired force and torque via the shafts 106 and 108, the wheels 110 and 112, and the wheels 102 and 104.

Figure 6:
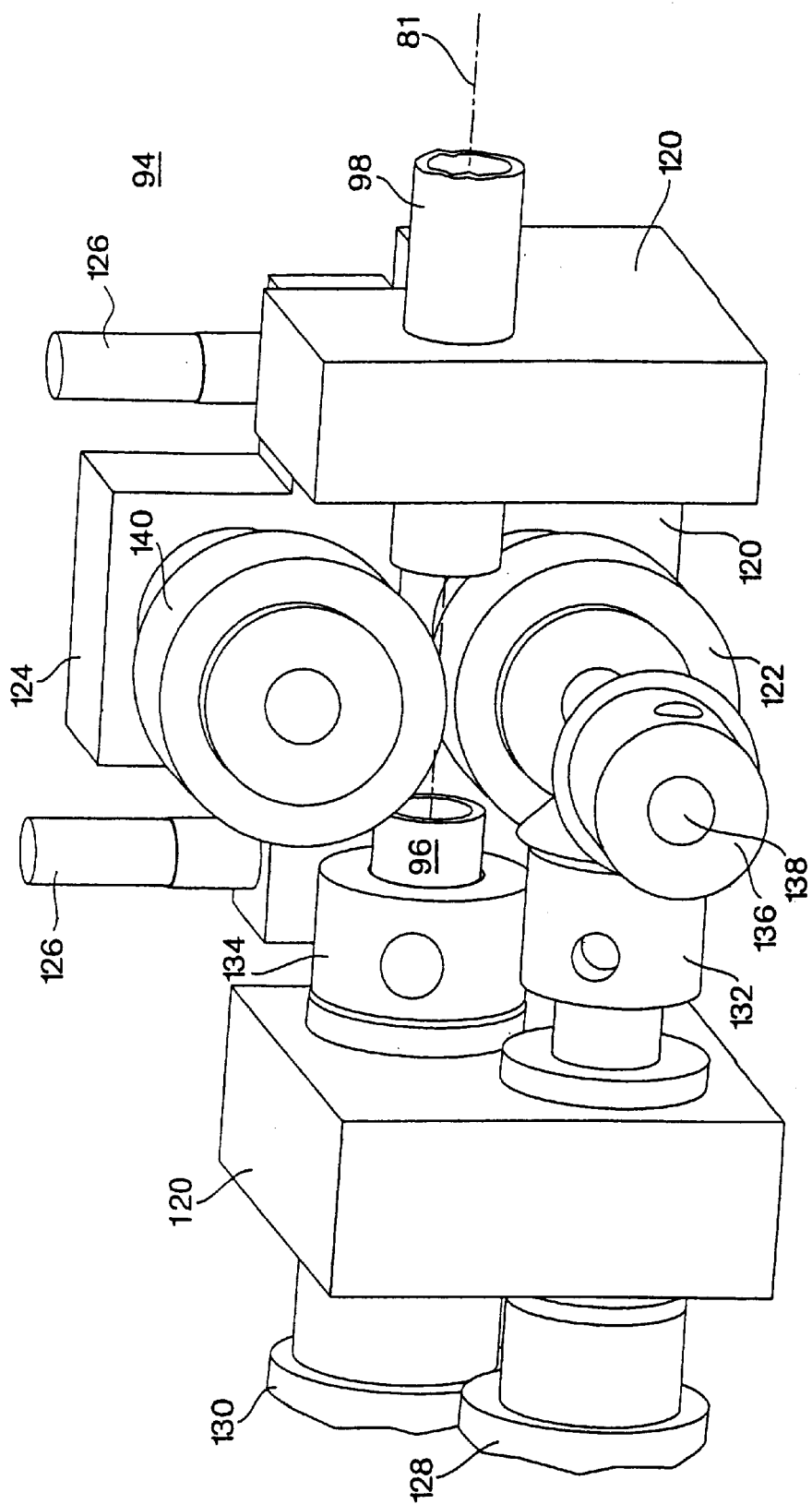
FIG. 6 is a front perspective diagram of a carriage assembly in the actuator of FIG. 5.
Figure 7:
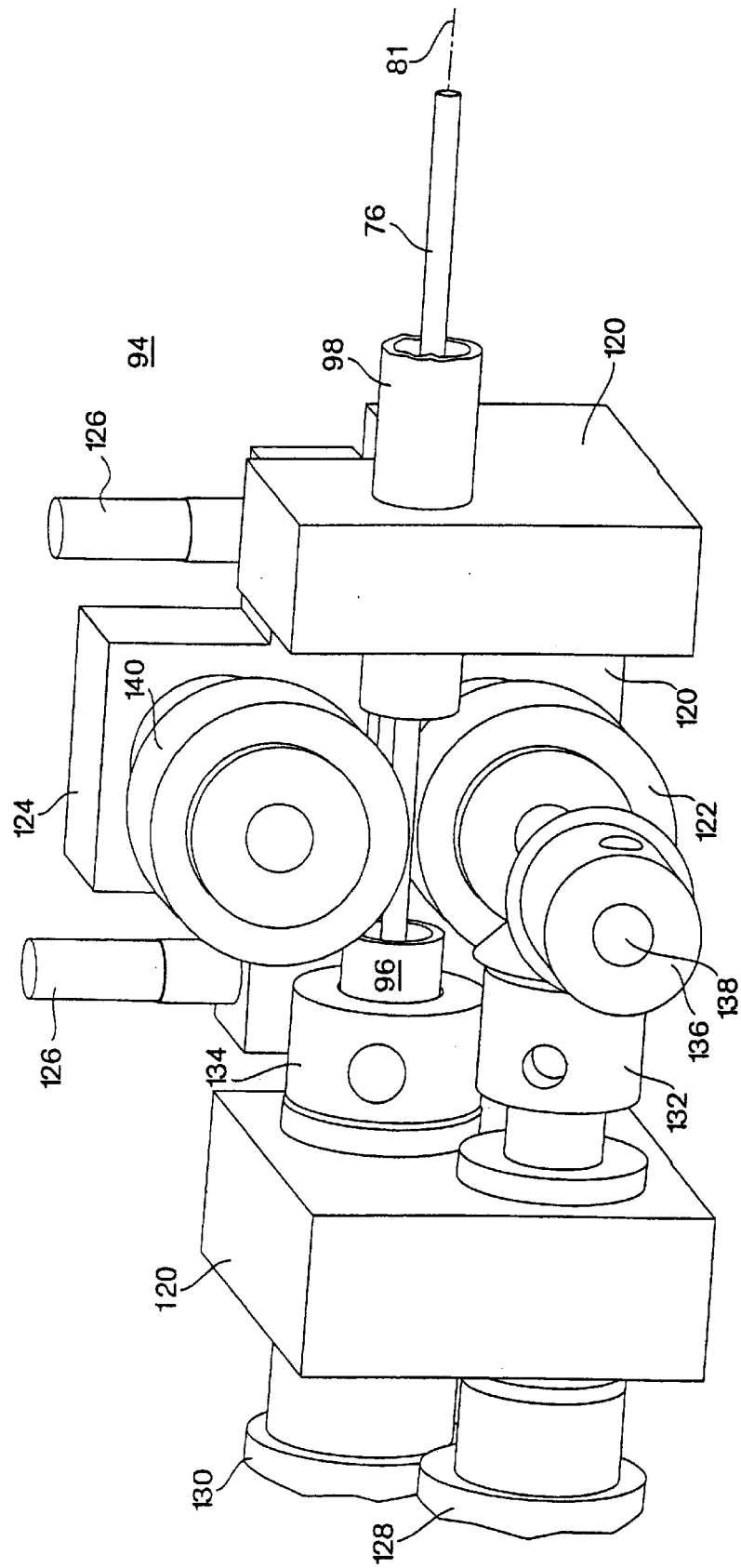
FIG. 7 is a front perspective diagram of the carriage assembly of FIG. 6 holding a tube from the actuator assembly of FIG. 3.
Figure 8:
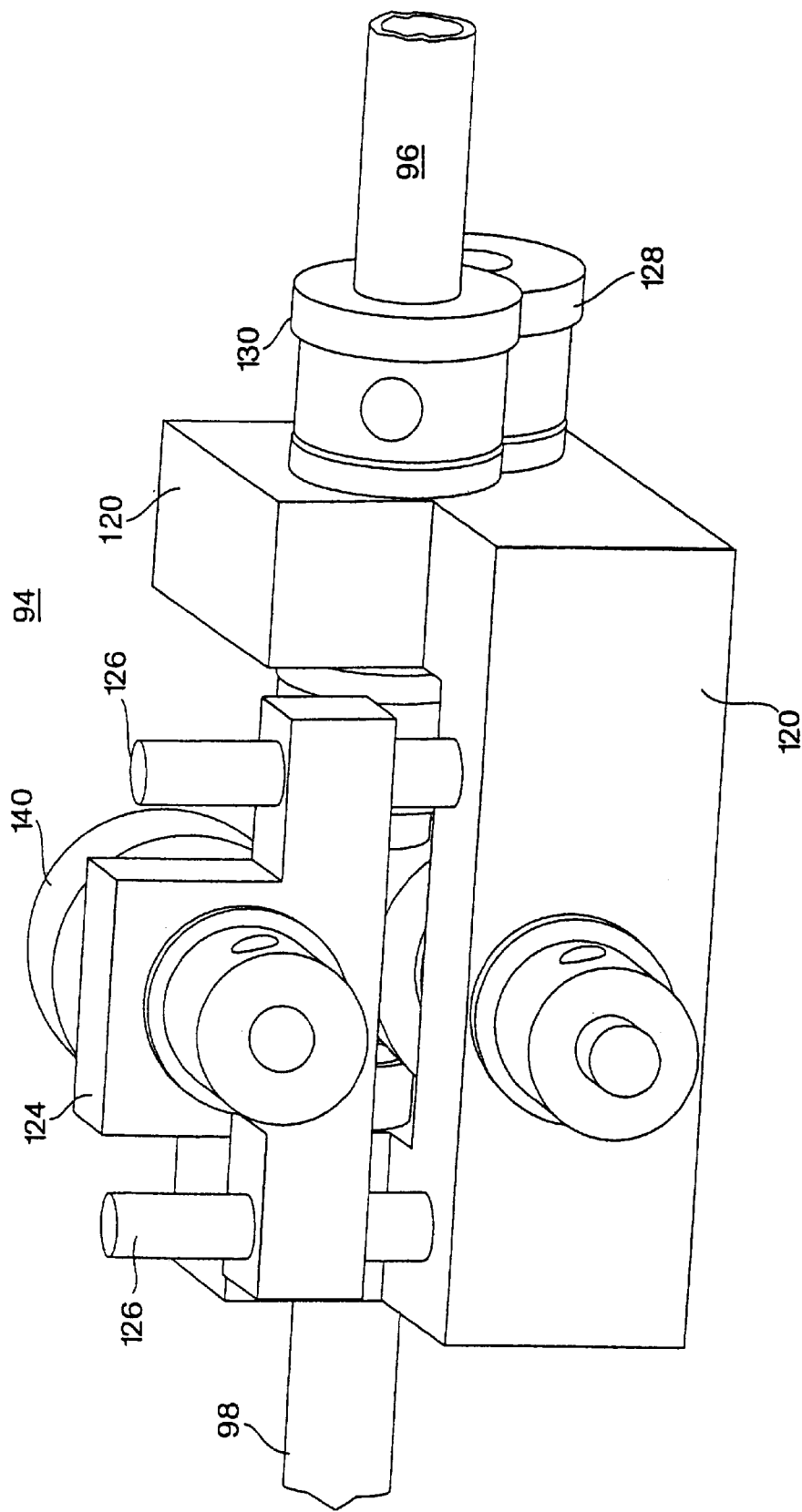
FIG. 8 is a rear perspective diagram of the carriage assembly of FIG. 6 showing a clamping member in an unclamped position.
Figure 9:
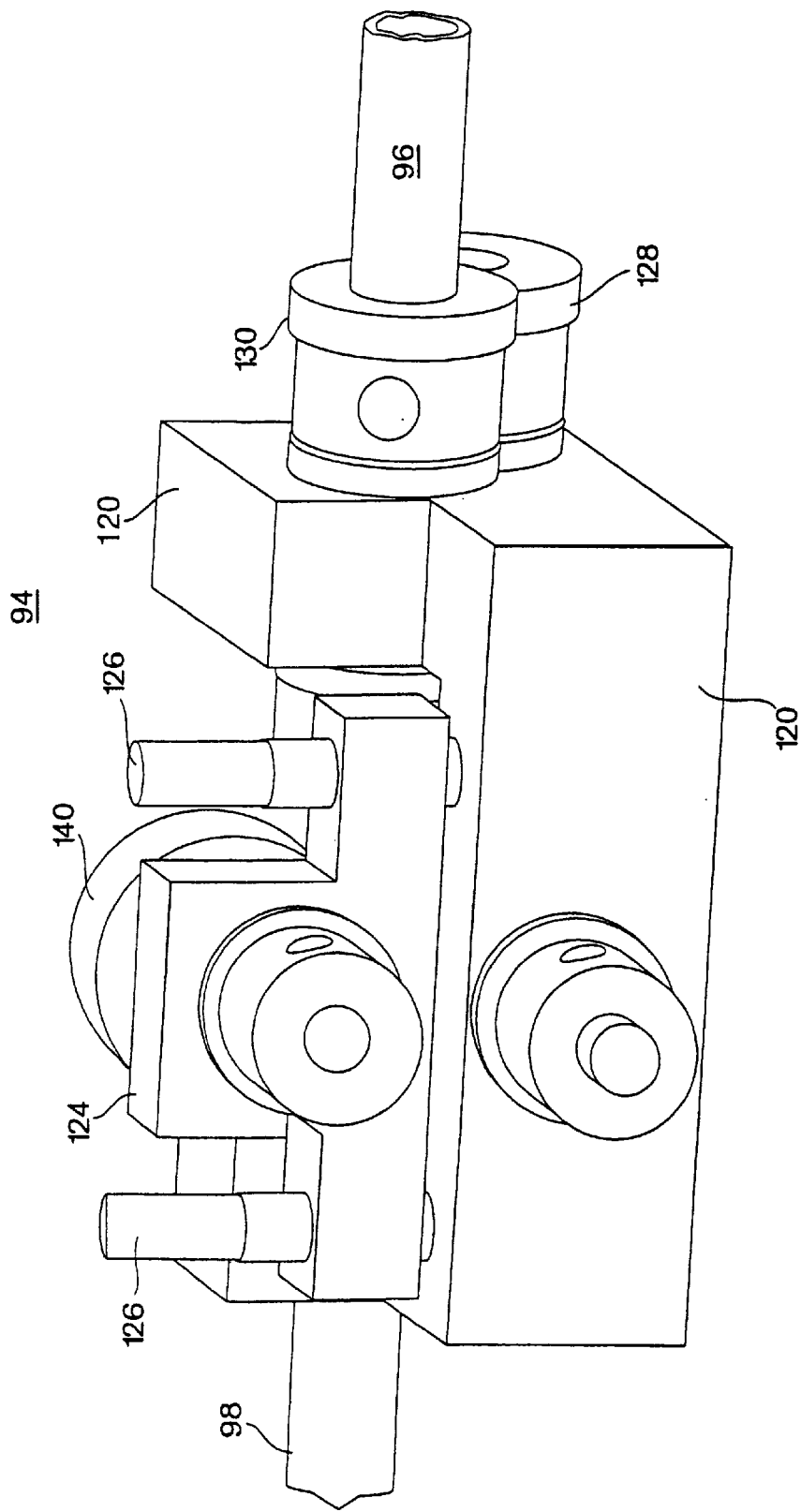
FIG. 9 is a rear perspective diagram of the carriage assembly of FIG. 8 showing the clamping member in a clamped position.

FIGS. 6–9 provide further views of the carriage assembly 94. FIG. 6 is a frontal perspective view of the carriage assembly 94 alone; FIG. 7 is frontal perspective view of the carriage assembly 94 in which wheels 140 and 122 engage a tube 76; FIG. 8 is a rear perspective view of the carriage member 94 in an unclamped position; and FIG. 9 is a rear perspective view of the carriage member 94 in a clamped position.

A three-sided carriage body 120 provides support for the following components: the shaft segments 96 and 98; a drive pinch wheel 122; a clamp member 124 supported by posts 126; mutually engaged wheels or gears 128 and 130; a miter wheel or gear 132 mounted on the same shaft as the wheel 128; and a collar 134 mounted on the same shaft as the wheel 130. The miter wheel 132 engages another miter wheel or gear 136 mounted on the same shaft 138 as the drive pinch wheel 122. An idle pinch wheel 140 is mounted on the clamp member 124.

The carriage body 120 is secured to the shaft segment 98 so that rotation of the shaft segment 98 about the axis 81 causes the carriage 94 to rotate about the axis 81. The wheel 130 and retaining collar 134 are mounted on the body 120 such that the wheel 130 can rotate about the axis 81 independent of rotation of the body 120 about the axis 81. The wheel 128 and miter wheel 132 are also mounted to rotate freely with respect to the body 120. Accordingly, the wheel 130 can impart rotation to the miter wheel 132 via wheel 128 independent of rotation of the body 120 about the axis 81.

In preparation for use of the actuator 70, the clamp member 124 is brought to the unclamped position depicted in FIG. 8. The tube 76, 78 or 80 is inserted through the shaft segments 96 and 98 along the actuation axis 81. The clamp member 124 is then brought to the clamped position of FIG. 9, such that the pinch wheels 122 and 140 engage the tube as shown in FIG. 7. Although not shown in the Figures, the posts 126 are preferably threaded in order to help secure the clamp member 124 to the body 120. A pair of springs is preferably disposed on each post 126, one between the body 120 and the clamp member 124 and one between the clamp member 124 and a retaining nut threaded onto the post 126. The clamp member 124 is moved between the clamped and unclamped positions by adjustment of the retaining nuts.

During operation of the actuator 70, rotation of the tube by a user results in rotation of the carriage assembly 94 about the axis 81. This rotation has two effects. The rotation is communicated to the encoder within the assembly 116 via shaft 98, wheels 104 and 112, and shaft 108 of FIG. 5. The rotation is also communicated to the encoder within assembly 114 by the following mechanism: The wheel 128 revolves about the axis 81 as the carriage 94 rotates. However, for pure rotation the wheel 128 does not rotate at all relative to wheel 120. Therefore the wheel 130 is caused to rotate by the non-rotating wheel 128. The rotation of wheel 130 is communicated to the encoder within assembly 114 by the shaft 96, the wheels 102 and 110, and the shaft 106 of FIG. 5.

Axial translation of the tube by a user causes the pinch wheels 122 to rotate, in turn causing miter wheels 136 and 132 to rotate. This rotation is communicated to the assembly 114 via wheels 128 and 130, along with the shaft 96, the wheels 102 and 110, and the shaft 106 of FIG. 5.

Haptic feedback is provided to the user by the application of axial forces and torques to the tube by the motors within the assemblies 114 and 116. The mechanical paths by which the torque of the motors is communicated to the tube are the reverse of the above-described paths by which user-generated movements are communicated to the encoders.

Figure 10:
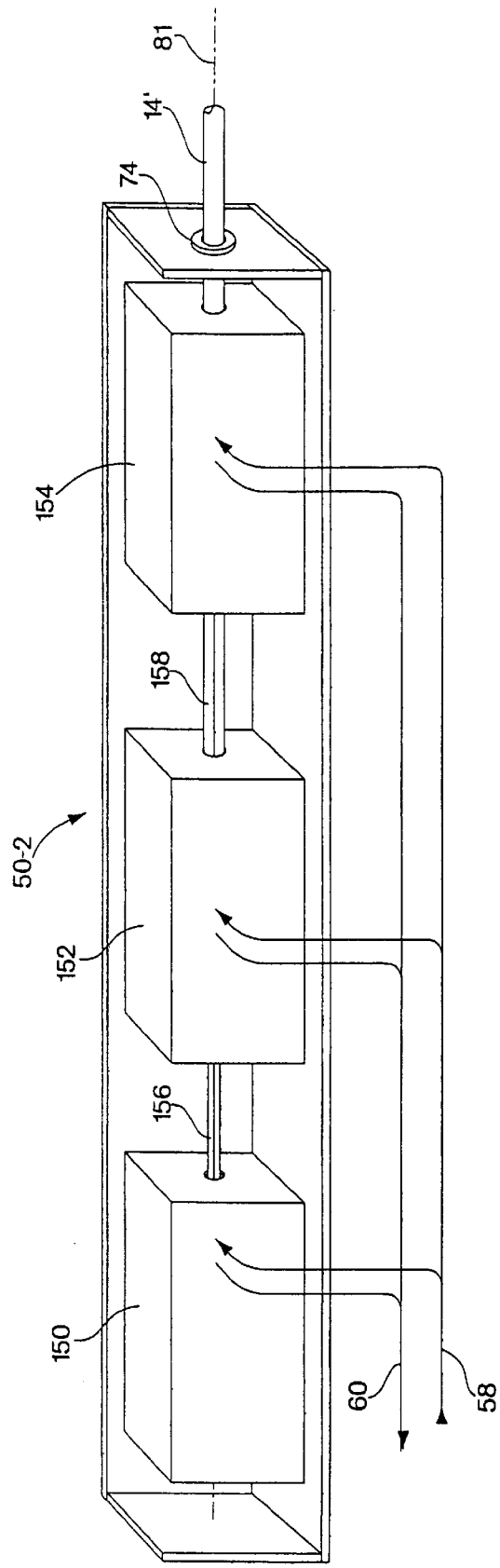
FIG. 10 is a perspective diagram of a second embodiment of an actuator assembly for the system of FIG. 2 including schematically-depicted actuators.

FIG. 10 shows a second embodiment of an actuator assembly 50-2 employing three actuators 150, 152, and 154 represented schematically. Like the actuator 70, the actuators 150, 152 and 154 both sense and cause translation and rotation. The actuators 150, 152 and 154 are generally similar to each other in construction. Each actuator engages a different-sized rigid tube having a square cross-section. The tube 156 shown in FIG. 10 is attached to the control 12' or catheter 12", and the tube 158 is attached to the control 10' or wire 10". A tube not shown in FIG. 10 within actuator 154 is attached to the control 14'. Because of the manner in which each actuators 150, 152 and 154 engages the corresponding tube, there are minor differences in their internal structure as described below.

Figure 11:
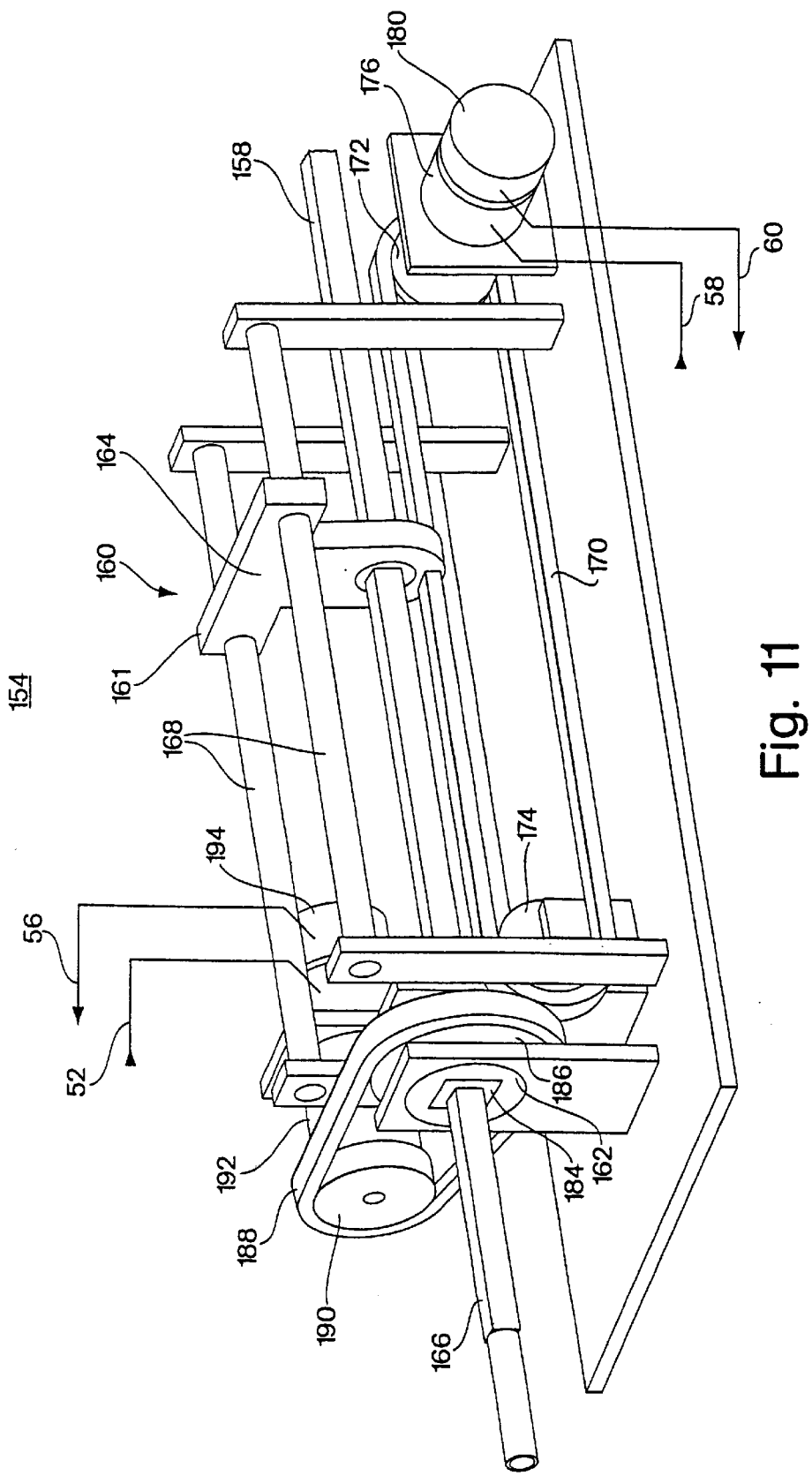
FIG. 11 is a perspective diagram of an actuator in the actuator assembly of FIG. 10.

FIG. 11 shows the actuator 154 used with the outermost catheter 14". The actuator 154 has a linear actuator 160 and a rotary actuator 162. The linear actuator 160 includes a generally T-shaped carrier 161 and a rotary bearing 164 that grips a tube 166 but allows the tube to be rotated about its longitudinal axis. The tube 166 is attached to the outermost catheter 14". The linear actuator 160 slides along rails 168, and is attached to a cable loop or belt of cable 170 extending between a drive pulley 172 and an idle pulley 174. The drive pulley 172 is rotated by a motor 176, and its rotary position is sensed by a position encoder or sensor 180. As the linear actuator 160 moves along the rails 168, the tube 166 moves along its axis while its rotational position is unconstrained.

The rotary actuator 162 includes a linear bearing 184 having a square opening through which the tube 166 passes. The linear bearing 184 tracks and controls the rotational position of the tube 166 while allowing the tube to be translated along its longitudinal axis. The rotary actuator 162 is also attached to a pulley 16 driven by a cable loop or belt 188, a drive pulley 190, and a motor 192. A rotary position encoder 194 senses the rotary position of the drive pulley 190. As the rotary actuator 162 rotates, the tube 166 also rotates along its longitudinal axis while its translational position is unconstrained. In the illustrated embodiment the tube 166 is constrained to rotate with rotary actuator 162 due to its square cross section. In alternative embodiments, the tubes within the actuators 150, 152 and 154 may have other cross-sectional shapes that constrain rotation, such as triangular, hexagonal, spline, etc.

The actuators 150 and 152 of FIG. 10 are essentially the same as the actuator 154, except that the bearings 162 and 164 are made to accommodate the narrower tubes 156 and 158. Also, it should be noted that the tube 158 is sufficiently narrower than the tube 166 to rotate independently within it, and likewise tube 156 rotates within tube 158. The belts 170 and 188 are preferably steel cables or bands riding within grooves in the rims of the pulleys 172, 174, 186, and 190. Alternatively, the pulleys may be sprocket-like wheels, and the belts 170 and 188 may be chain or of alternative construction with an undulating inner surface for engaging the teeth on the sprocket-like pulleys.

Figure 12:
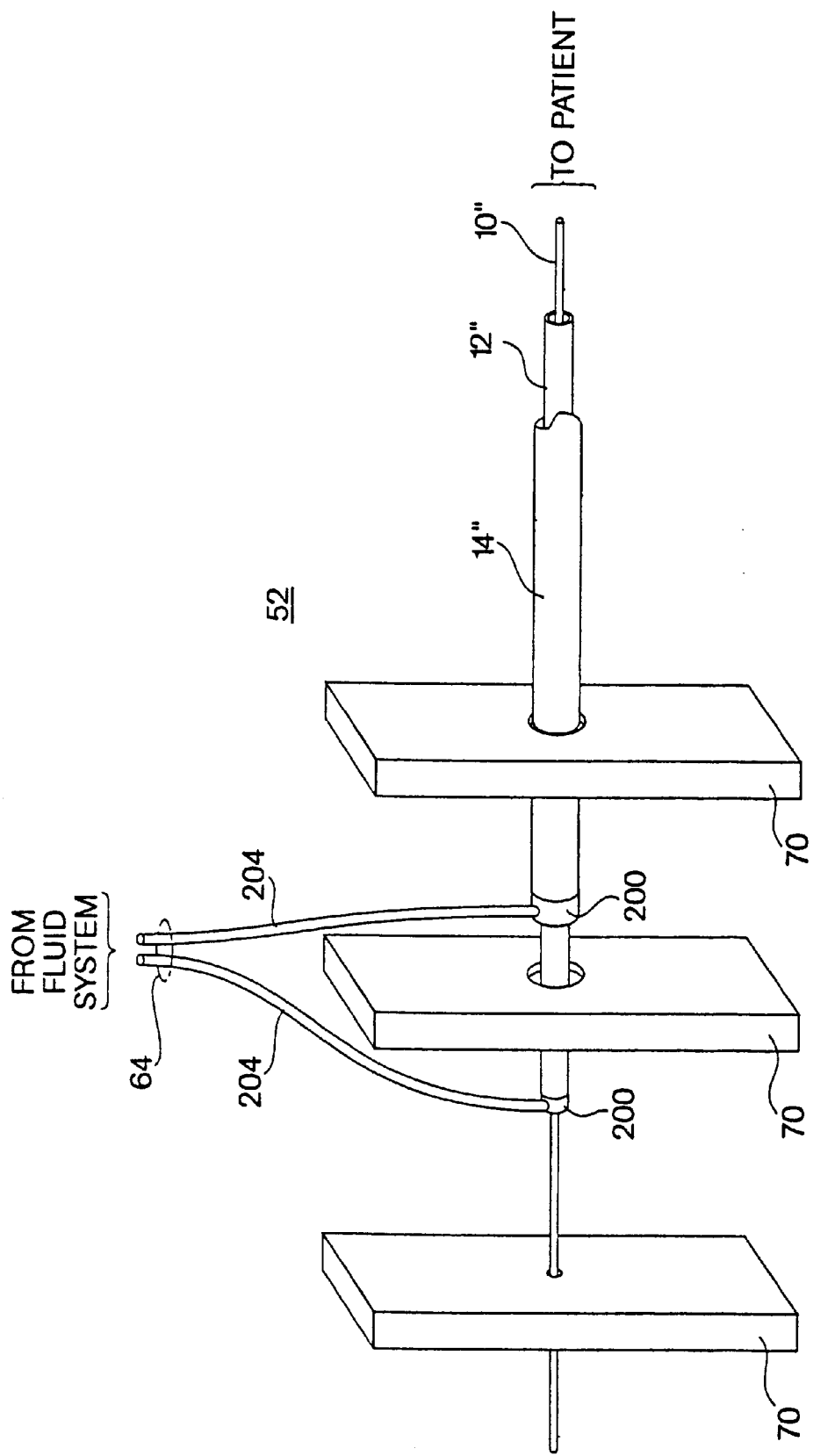
FIG. 12 is a diagram of a slave actuator in the system of FIG. 2.

FIG. 12 shows the slave actuator 52 of FIG. 2, including features of the actuator 52 that enable the injection of fluids into the patient 54. Like the master actuator 50, the slave actuator 52 includes three actuators, for example the actuators 70 of FIG. 3. Each actuator 70 engages a corresponding one of the wire 10" and the catheter 12" or 14", and is used to cause translational and rotational movement of the corresponding wire or catheter as previously described. The catheters 12" and 14" each have fluid couplings 200 at one end. The tubes 64 from the fluid system 62 of FIG. 2 are connected to a set of valves 202, which in turn are connected to the couplings 200 by tubes 204. The valves 202 are used to control the flow of fluids from the fluid system 62 of FIG. 2 to the patient 54. The coupling 200 on catheter 12" provides a fluid-tight seal with the control 10", and likewise the coupling 200 on catheter 14" provides a fluid-tight seal with the catheter 12".

The foregoing has described a master/slave control system that enables a user to remotely manipulate a tubular object such as a catheter and that provides haptic or tactile feedback to the user It will be apparent to those skilled in the art that modification to and variation of the above-described methods and apparatus are possible without departing from the inventive concepts disclosed herein. Accordingly, the invention should be viewed as limited solely by the scope and spirit of the appended claims.

What is claimed is:

1. Apparatus for manipulating a generally cylindrical medical tool having a longitudinal axis and being adapted for insertion in a patient in a minimally invasive medical procedure, comprising:

at least one generally cylindrical control having a longitudinal axis, wherein the control may be manipulated by a user so as to cause translation of the control along the axis and rotation of the control about the axis;

a first actuator comprising sensors coupled to the control and motors mechanically engaging the control, the first actuator being operative to generate first electrical sensor signals indicative of the translational and rotational movement of the control in response to the translation and rotation of the control with respect to the axis thereof by the user, the first actuator also being operative to cause translation and rotation of the control with respect to the axis thereof in response to selective application of first electrical motor drive signals to the motors;

a second actuator comprising sensors adapted to be coupled to the tool and motors mechanically engaging the tool, the second actuator being operative to generate second electrical sensor signals indicative of the translational and rotational movement of the tool with respect to the axis thereof, the second actuator also being operative to cause translation and rotation of the tool with respect to the axis thereof in response to selective application of second electrical motor drive signals to the motors; and an electronic interface operative to receive the first and second electrical sensor signals as inputs and to generate the first and second motor drive signals to cause movement of the tool in response to movement of the control by the user and to provide haptic feedback to the user via the control in response to movement of the tool inside the patient.

2. Apparatus according to claim 1, wherein the electronic interface includes a processor operative to execute a master-slave control program to cause the movement of the tool and to provide the haptic feedback to the user.

3. Apparatus according to claim 2, wherein the master-slave control program is a position-matching type of control program.

4. Apparatus according to claim 1, wherein the tool is a first catheter and the control is a first tubular control, and further comprising:

a second catheter concentric with the first catheter;

a second tubular control concentric with the first tubular control;

sensors within the first actuator coupled to the second tubular control and motors within the first actuator mechanically engaging the second tubular control; and sensors within the second actuator coupled to the second catheter and motors within the second actuator mechanically engaging the second catheter;

and wherein (i) the first actuator is operative to generate third electrical sensor signals indicative of the translational and rotational movement of the second tubular control in response to the translation and rotation of the second tubular control with respect to the axis thereof by the user, (ii) the first actuator is also operative to cause translation and rotation of the second tubular control with respect to the axis thereof in response to selective application of third electrical motor drive signals to the motors, (iii) the second actuator is operative to generate fourth electrical sensor signals indicative of the translational and rotational movement of the second catheter with respect to the axis thereof, (iv) the second actuator is also operative to cause translation and rotation of the second catheter with respect to the axis thereof in response to selective application of fourth electrical motor drive signals to the motors, and (v) the electronic interface is operative to receive the third and fourth electrical sensor signals as inputs and to generate the third and fourth motor drive signals to cause movement of the second catheter in response to movement of the second tubular control by the user and to provide haptic feedback to the user in response to movement of the second catheter inside the patient.

5. Apparatus according to claim 4, further comprising:

a wire concentric with the second catheter;

a third tubular control concentric with the second tubular control;

sensors within the first actuator coupled to the third tubular control and motors within the first actuator mechanically engaging the third tubular control; and sensors within the second actuator coupled to the wire and motors within the second actuator mechanically engaging the wire;

and wherein (i) the first actuator is operative to generate third electrical sensor signals indicative of the translational and rotational movement of the second tubular control in response to the translation and rotation of the second tubular control with respect to the axis thereof by the user, (ii) the first actuator is also operative to cause translation and rotation of the second tubular control with respect to the axis thereof in response to selective application of third electrical motor drive signals to the motors, (iii) the second actuator is operative to generate fourth electrical sensor signals indicative of the translational and rotational movement of the wire with respect to the axis thereof, (iv) the second actuator is also operative to cause translation and rotation of the wire with respect to the axis thereof in response to selective application of fourth electrical motor drive signals to the motors, and (v) the electronic interface is operative to receive the third and fourth electrical sensor signals as inputs and to generate the third and fourth motor drive signals to cause movement of the wire in response to movement of the second tubular control by the user and to provide haptic feedback to the user in response to movement of the wire inside the patient.

6. Apparatus according to claim 1, wherein the electronic interface is operative to carry out one or more of force scaling, position scaling, and tremor reduction in moving the tool in response to movement of the control by the user.

7. Apparatus according to claim 1, wherein the electronic interface is operative to provide a preprogrammed tool motion sequence is response to a control signal activated by the user.

8. Apparatus according to claim 1, wherein the tool is a catheter.

9. Apparatus according to claim 1, wherein the tool is a catheter, and further comprising:
   a sealed fluid coupling mounted on the catheter at the end thereof outside the patient; and
   a fluid system connected to the coupling for the delivery of a fluid to the catheter, the fluid system including a valve operable by the user to control fluid flow between the fluid system and the catheter.

10. A system for manipulating an object comprising:
    a moveable controller;
    a moveable physical object;
    a sensor configured to detect movement of the moveable controller;
    an input device configured to receive a user instruction;
    a drive signal generator configured to generate first drive signals corresponding to the detected controller movement and to generate second drive signals based upon the received user instruction; and
    an actuator configured to move the movable object in accordance with the generated first and the second drive signals.

11. A system according to claim 10, wherein:
    the controller movement is in a direction;
    the detected movement is a detected amount of controller movement in the direction;
    the generated first drive signals correspond to the detected amount of controller movement; and
    the movable object is moved in the direction and by an amount which is one of equal to and less than the detected amount of controller movement.

12. A system according to claim 10, wherein the movement of the controller is one of a translation and a rotation.

13. A system according to claim 10, wherein the object is moved in a predetermined sequence in accordance with the generated second drive signals.

14. A system for manipulating an object, comprising:
    a movable controller;
    a movable physical object;
    a sensor configured to detect movement of the movable controller;
    an input device configured to receive a user instruction;
    a drive signal generator configured to generate first drive signals corresponding to the detected controller movement and second drive signals based upon the received user instruction;
    an actuator configured to move the movable object in accordance with the generated first drive signals; and
    a fluid valve configured to control a flow of fluid to the movable object in accordance with the generated second drive signals.

15. A system according to claim 14, wherein the fluid is controlled to flow in a predetermined manner in accordance with the generated second drive signals.

16. A system for manipulating an object, comprising:
    a movable controller;
    a movable physical object;
    a first sensor configured to detect movement of the movable controller;
    a second sensor configured to detect movement of the movable object; and
    a drive signal generator configured to generate first drive signals corresponding to the detected controller movement and second drive signals corresponding to the detected object movement;
    a first actuator configured to move the movable object in accordance with the generated first drive signals; and
    a second actuator configured to move the movable controller in accordance with the generated second drive signals.

17. A system for manipulating an object, comprising:
    a movable controller;
    a movable physical object;
    a first sensor configured to detect movement of the movable controller;
    a second sensor configured to detect a resistance to movement of the movable object;
    a drive signal generator configured to generate first drive signals corresponding to the detected controller movement and second drive signals corresponding to the detected resistance to the object movement;
    a first actuator configured to move the movable object in accordance with the generated first drive signals; and
    a second actuator is configured to resist the movement of the movable controller in accordance with the generated second drive signals.

18. A system for manipulating an object, comprising:
    a movable controller;
    a movable physical object;
    a sensor configured to detect movement of the movable controller;
    a drive signal generator configured to filter the detected controller movement and to generate drive signals corresponding to the filtered controller movement.

19. A method for manipulating an object, comprising the steps of:
    detecting movement of a controller;
    generating first drive signals corresponding to the detected controller movement;

generating second drive signals based on a user command; and physically moving an object in accordance with the generated first and the generated second drive signals.

20. A method for manipulating an object, comprising the steps of:

detecting movement of a controller;

generating first drive signals corresponding to the detected controller movement;

physically moving an object in accordance with the generated first drive signals;

detecting the movement of the object;

generating second drive signals corresponding to the detected object movement; and moving the controller in accordance with the generated second drive signals.

21. A method for manipulating an object, comprising the steps of:

detecting movement of a controller;

generating first drive signals corresponding to the detected controller movement;

physically moving an object in accordance with the generated first drive signals;

detecting a resistance to the movement of the object;

generating second drive signals corresponding to the detected resistance to the object movement; and resisting the movement of the controller in accordance with the generated second drive signals.

22. A method for manipulating an object, comprising the steps of:

detecting movement of a controller;

generating first drive signals corresponding to the detected controller movement;

generating second drive signals based upon a user command;

physically moving an object in accordance with the generated first drive signals; and controlling a flow of fluid to the object in accordance with the generated second drive signals.

23. A method for manipulating an object, comprising the steps of:

detecting movement of a controller;

filtering the detected controller movement;

generating drive signals so as to correspond to the filtered controller movement; and physically moving an object in accordance with the generated drive signals.

* * * * *